(12) United States Patent
Anayama et al.

(10) Patent No.: US 9,121,833 B2
(45) Date of Patent: Sep. 1, 2015

(54) DEFECT INSPECTING APPARATUS

(75) Inventors: Kazunori Anayama, Osaka (JP);
Toshiyuki Suzuma, Osaka (JP);
Yoshiyuki Nakao, Osaka (JP); Masami Ikeda, Osaka (JP); Kenta Sakai, Osaka (JP)

(73) Assignee: NIPPON STEEL & SUMITOMO METAL CORPORATION, Tokyo (JP)

(*) Notice: Subject to any disclaimer, the term of this patent is extended or adjusted under 35 U.S.C. 154(b) by 635 days.

(21) Appl. No.: 13/551,014

(22) Filed: Jul. 17, 2012

(65) Prior Publication Data

US 2012/0327217 A1    Dec. 27, 2012

Related U.S. Application Data

(63) Continuation of application No. PCT/JP2011/051583, filed on Jan. 27, 2011.

(30) Foreign Application Priority Data

Jan. 29, 2010    (JP) .................................. 2010-017909

(51) Int. Cl.
*H04N 7/18*      (2006.01)
*G01N 21/952*    (2006.01)

(52) U.S. Cl.
CPC .................................. *G01N 21/952* (2013.01)

(58) Field of Classification Search
None
See application file for complete search history.

(56) References Cited

FOREIGN PATENT DOCUMENTS

| | | |
|---|---|---|
| JP | 60-250235 | 12/1985 |
| JP | 61-225610 | 10/1986 |
| JP | 62-069113 | 3/1987 |
| JP | 63-191007 | 8/1988 |
| JP | 02-058588 | 2/1990 |
| JP | 03-135753 | 6/1991 |
| JP | 2005-181001 | 7/2005 |
| JP | 2007-010393 | 1/2007 |
| JP | 2010-038554 | 2/2010 |
| JP | 2010-210292 | 9/2010 |
| WO | 2009/119713 | 10/2009 |

*Primary Examiner* — Mehrdad Dastouri
*Assistant Examiner* — James Anderson, II
(74) *Attorney, Agent, or Firm* — Clark & Brody

(57) ABSTRACT

A defect inspecting apparatus includes a first light source, a first image capture device that receives the reflection light emitted from the first light source and reflected by the outer peripheral surface of a lip part to grab the image of the outer peripheral surface of the lip part, a second light source, a second image capture device 8 that receives the reflection light emitted from the second light source and reflected by a load face to grab the image of the load face, a third light source, a third image capture device that receives the reflection light emitted from the third light source and reflected by a thread bottom face inspection zone 106 to grab the image of the thread bottom face inspection zone, and an inspection device for inspecting defects by processing the captured images grabbed by the first to third image capture devices.

7 Claims, 11 Drawing Sheets

Fig. 5

| -3 | -2 | 0 | 2 | 3 |
|----|----|---|---|---|
| -3 | -2 | 0 | 2 | 3 |
| -3 | -2 | 0 | 2 | 3 |

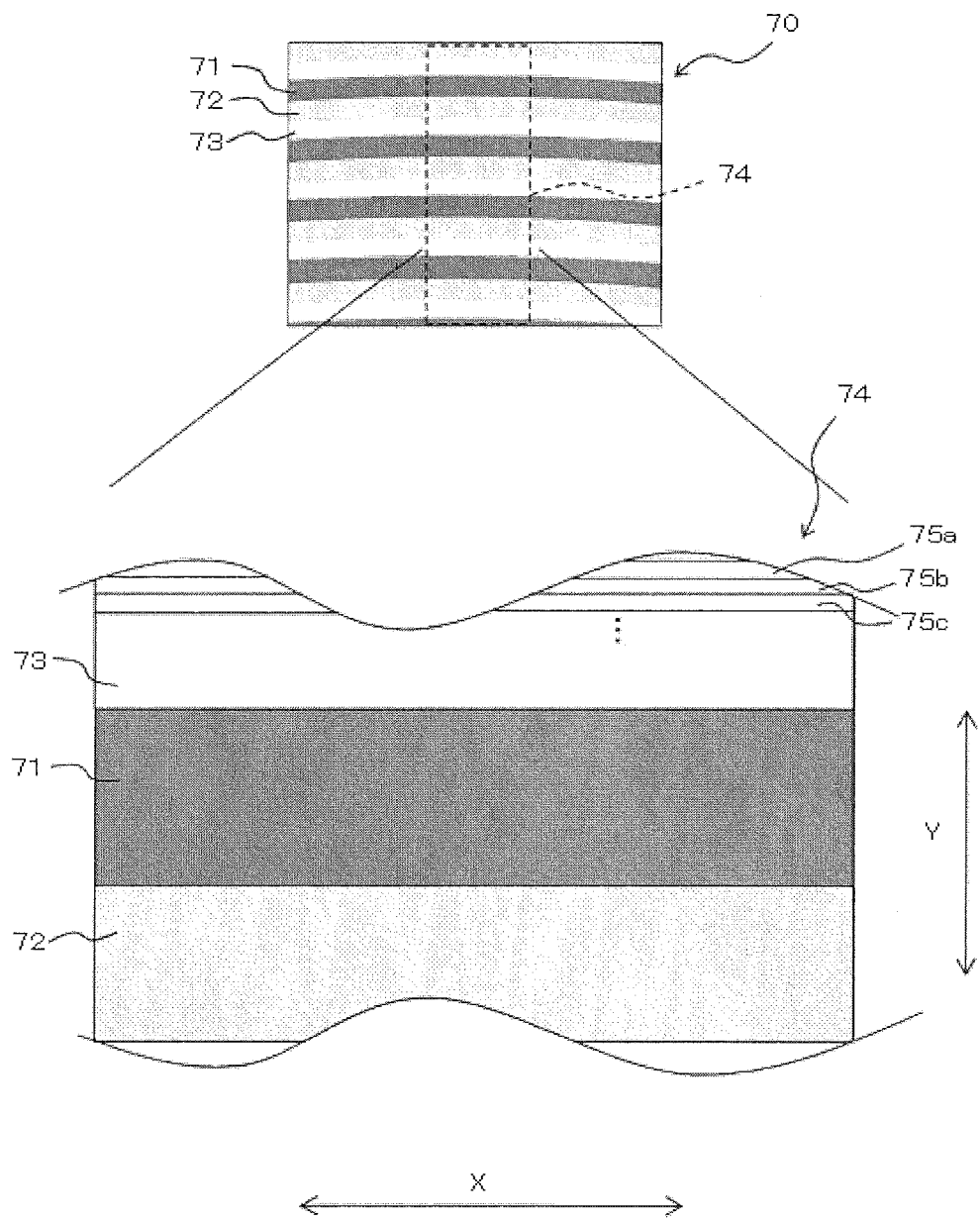

DEFECT INSPECTING APPARATUS

TECHNICAL FIELD

The present invention relates to a defect inspecting apparatus for inspecting a defect on the outer peripheral surface of a pipe or tube. Hereinafter, "pipe or tube" is referred to as "pipe" when deemed appropriate.

BACKGROUND ART

A defect inspecting apparatus for inspecting a defect on the outer peripheral surface of a pipe has been disclosed in Patent Literature 1. The defect inspecting apparatus disclosed in Patent Literature 1 includes a light source for illuminating the outer peripheral surface of the pipe, an image capture device for grabbing the image of the outer peripheral surface of the pipe by receiving the reflection light reflected by the outer peripheral surface of the pipe, and an inspection device for inspecting a defect on the outer peripheral surface of the pipe by processing the captured image grabbed by the image capture device.

Pipes subjected to such a defect inspection may include a steel pipe for oil well casing, tubing and drilling (hereinafter, referred to as an oil well steel pipe) as shown in FIG. 10. In the end portion of an oil well steel pipe 200, an external thread part 201 and a lip part 202 are provided in that order from the inside in the pipe axis direction. The lip part 202 is tapered such that the dimension in the direction perpendicular to the pipe axis direction decreases outwardly (to the pipe end side) in the pipe axis direction.

In using the oil well steel pipe 200, two or more pipes are joined by a joint 210. On the inner peripheral surface of the joint 210, an internal thread part 211 capable of threadedly engaging with the external thread part 201 of the oil well steel pipe 200 and a no-thread part 212 are provided. When the external thread part 201 of the oil well steel pipe 200 and the internal thread part 211 of the joint 210 are threadedly engaged with each other, the outer peripheral surface of the lip part 202 comes into close contact with the no-thread part 212 of the joint 210. By the close contact of the outer peripheral surface of the lip part 202 with the no-thread part 212, oil leakage from between the oil well steel pipe 200 and the joint 210 is prevented when two or more oil well steel pipes 200 are joined in use.

If a defect is present on the outer peripheral surface of the lip part 202, which is in close contact with the no-thread part 212, oil leakage may occur from between the oil well steel pipe 200 and the joint 210. Also, in the case where the oil well steel pipes 200 are joined in use, a high stress may develop on a load face 203 of the external thread part 201 and in a thread bottom face inspection zone 206. The load face 203 is an inside face (on the side opposite to the pipe end side) of opposing side faces in the pipe axis direction of a thread ridge part 207. The thread bottom face inspection zone 206 is a zone of a thread bottom face 204 ranging from a boundary part 205 between the load face 203 and the thread bottom face 204 to a portion 208 of the thread bottom face 204 spaced apart inwardly by a predetermined distance from the boundary part 205 in the pipe axis direction. Since a high stress develops on the load face 203 and in the thread bottom face inspection zone 206 as described above, if a defect is present on the load face 203 or in the thread bottom face inspection zone 206, the oil well steel pipe 200 may be damaged.

For this reason, any defect on the outer peripheral surface of the lip part 202, on the load face 203, and in the thread bottom face inspection zone 206 must be inspected with high accuracy.

As shown in FIG. 10, some oil well steel pipes 200 have the load face 203 inclined inwardly in the pipe axis direction relative to the vertical plane perpendicular to the pipe axis direction. As shown in FIG. 11, the direction of the optical axis of an image capture device 222 that the apparatus of Patent Literature 1 has coincides with the direction perpendicular to the pipe axis direction. The image capture device 222 of the apparatus of Patent Literature 1, in which the direction of optical axis coincides with the direction perpendicular to the pipe axis direction, cannot grab the image of the load face 203 inclined inwardly in the pipe axis direction. Therefore, the apparatus of Patent Literature 1 cannot inspect a defect on the load face 203 inclined inwardly in the pipe axis direction.

Also, if the load face 203 is inclined inwardly in the pipe axis direction, in the pipe axis direction, the load face 203 is present at the same position as a portion close to the boundary part 205 of the thread bottom face inspection zone 206. Due to the presence of the load face 203, the reflection light reflected to the direction perpendicular to the pipe axis direction by the portion close to the boundary part 205 of the thread bottom face inspection zone 206 enters the load face 203. Therefore, the image capture device 222 of the apparatus of Patent Literature 1, in which the direction of optical axis coincides with the direction perpendicular to the pipe axis direction as described above, cannot grab the image of the entire zone of the thread bottom face inspection zone 206 (i.e. cannot grab the image of the portion close to the boundary part 205 of the thread bottom face inspection zone 206). Therefore, the apparatus of Patent Literature 1 cannot inspect a defect over the entire zone of the thread bottom face inspection zone 206 if the load face 203 is inclined inwardly in the pipe axis direction.

Furthermore, Patent Literature 1 does not describe the inspection of any defect on the outer peripheral surface of the lip part 202.

CITATION LIST

Patent Literature

[Patent Literature 1] JP2-58588B

SUMMARY OF INVENTION

Technical Problem

An objective of the present invention is to provide a defect inspecting apparatus capable of inspecting defects on a load face and in a thread bottom face inspection zone of a pipe or tube in which the load face is inclined inwardly in the pipe or tube axis direction, and also capable of inspecting a defect on the outer peripheral surface of a lip part.

Solution to Problem

The present invention provides a defect inspecting apparatus for inspecting a defect on the outer peripheral surface of a pipe or tube in which in the end portion thereof, an external thread part and a lip part are provided in that order from the inside (the side opposite to the pipe or tube end side) in the pipe or tube axis direction; a load face of the external thread part is inclined inwardly in the pipe or tube axis direction relative to the vertical plane perpendicular to the pipe or tube axis direction; and the lip part is tapered such that the dimension in the direction perpendicular to the pipe or tube axis direction decreases outwardly (to the pipe or tube end side) in the pipe or tube axis direction, wherein the defect inspecting apparatus includes a first light source for illuminating the outer peripheral surface of the lip part, in which the optical axis thereof is inclined through an angle A satisfying formula (1) outwardly in the pipe or tube axis direction relative to the vertical plane; a first image capture device that is attached to the first light source so that the optical axis thereof is coaxial with the optical axis of the first light source, and receives the reflection light emitted from the first light source and reflected by the outer peripheral surface of the lip part to grab the image of the outer peripheral surface of the lip part; a second light source for illuminating the load face; a second image capture device that is attached to the second light source, and has the optical axis adjusted so that the reflection light emitted from the second light source and reflected by the load face to the direction inclined through an angle B satisfying formula (2) inwardly in the pipe or tube axis direction relative to the vertical plane can be received, and the reflection light is received to grab the image of the load face; a third light source for illuminating a thread bottom face inspection zone ranging from a boundary part between the load face and the thread bottom face of the external thread part to a portion of the thread bottom face spaced apart inwardly by a predetermined distance from the boundary part in the pipe or tube axis direction; a third image capture device that is attached to the third light source, and has the optical axis adjusted so that the reflection light emitted from the third light source and reflected by the thread bottom face inspection zone to the direction inclined through an angle C satisfying formula (3) inwardly in the pipe or tube axis direction relative to the vertical plane can be received, and the reflection light is received to grab the image of the thread bottom face inspection zone; and an inspection device for inspecting defects on the outer peripheral surface of the lip part, on the load face, and in the thread bottom face inspection zone by processing the captured images grabbed by the first to third image capture devices:

$$a-45 \leq A \leq a+45 \quad (1)$$

$$b < B \leq c \quad (2)$$

$$b < C \leq d \quad (3)$$

$a°$ being an angle (smaller than 90°) faulted between the outer peripheral surface of the lip part and the pipe or tube axis direction in the cross section including the pipe or tube axis;

$b°$ being an angle (smaller than 90°) formed between the load face and the vertical plane in the cross section including the pipe or tube axis;

$c°$ being an angle (smaller than 90°) formed between a straight line and the vertical plane in the cross section including the pipe or tube axis, the straight line connecting the boundary part between the load face and the thread bottom face to a front end part of an insertion face of the external thread part, the insertion face connecting with an inside end part in the pipe or tube axis direction of the thread bottom face; and $d°$ being an angle (smaller than 90°) formed between a straight line and the vertical plane in the cross section including the pipe or tube axis, the straight line connecting an inside end part in the pipe or tube axis direction of the thread bottom face inspection zone to the front end part of the insertion face of the external thread part, the insertion face connecting with an inside end part in the pipe or tube axis direction of the thread bottom face.

First, explanation is given of the fact that the defect inspecting apparatus in accordance with the present invention can inspect a defect on the outer peripheral surface of the lip part. The optical axis of the first light source for illuminating the outer peripheral surface of the lip part is inclined through the angle A satisfying formula (1) outwardly in the pipe or tube axis direction relative to the vertical plane perpendicular to the pipe or tube axis direction. The case where the angle A is a negative angle implies that the optical axis of the first light source is inclined through an angle A by its absolute value inwardly in the pipe or tube axis direction relative to the vertical plane. Since the optical axis of the first light source is inclined through the angle A outwardly in the pipe or tube axis direction relative to the vertical plane as described above, it follows that the light emitted from the first light source enters the outer peripheral surface of the lip part from the direction inclined through an angle not larger than 45° relative to the direction normal to the outer peripheral surface of the lip part. Therefore, the angle formed between the direction from which the light emitted from the first light source enters the outer peripheral surface of the lip part and the specular direction (the direction of the light reflected by the outer peripheral surface of the lip part so that the angle of incidence and the angle of reflection are equal to each other) that is emitted from the first light source, entering the outer peripheral surface of the lip part, and is specularly reflected by the outer peripheral surface thereof is 90° at the maximum. Since the optical axis of the first image capture device is coaxial with the optical axis of the first light source, the direction of the optical axis of the first image capture device coincides with the direction from which the light emitted from the first light source enters the outer peripheral surface of the lip part. Therefore, the angle formed between the direction of the optical axis of the first image capture device and the specular direction is not larger than 90°. The quantity of light reflected by the outer peripheral surface thereof tends to increase as the reflection direction is closer to the specular direction. Therefore, the first image capture device such that the angle formed between the specular direction and the direction of optical axis is not larger than 90° can receive the reflection light, which is emitted from the first light source and reflected by the outer peripheral surface of the lip part, in large amounts, so that the image of the outer peripheral surface of the lip part can be grabbed clearly. Since the first image capture device can grab the image of the outer peripheral surface of the lip part clearly, the defect inspecting apparatus in accordance with the present invention can inspect a defect on the outer peripheral surface of the lip part by processing the captured image grabbed by the first image capture device.

Next, explanation is given of the fact that the defect inspecting apparatus in accordance with the present invention can inspect a defect on the load face with high accuracy. The defect inspecting apparatus in accordance with the present invention includes the second light source and the second image capture device. The second light source illuminates the load face. The illumination of the load face provided by the second light source has two implications; the light emitted from the second light source is caused to enter the load face without being reflected by any portion of the pipe or tube, and the light emitted from the second light source is caused to enter the load face after being reflected by a portion (for example, the thread bottom face) of the pipe or tube.

For the second image capture device, the optical axis is adjusted so that the reflection light that is emitted from the second light source and reflected by the load face to the direction inclined through the angle B satisfying formula (2) inwardly in the pipe or tube axis direction relative to the vertical plane can be received. The load face is inclined through b° inwardly in the pipe or tube axis direction relative to the vertical plane. Therefore, all of the reflection lights reflected by the load face are reflected by the load face to the direction inclined through an angle larger than b° inwardly in the pipe or tube axis direction relative to the vertical plane. Also, if the reflection direction of the reflection light reflected by the boundary part between the load face and the thread bottom face is the direction inclined through an angle larger than c° inwardly in the pipe or tube axis direction relative to the vertical plane, the reflection light enters the insertion face connecting with an inside end part in the pipe or tube axis direction of the thread bottom face. Therefore, the second image capture device the optical axis of which is adjusted so as to be capable of receiving the reflection light reflected by the load face to the direction inclined through the angle B satisfying formula (2) inwardly in the pipe or tube axis direction relative to the vertical plane can receive the reflection lights reflected by the positions of the load face, and therefore can grab the image of the load face. Since the second image capture device can grab the image of the load face, the defect inspecting apparatus in accordance with the present invention can inspect a defect on the load face with high accuracy by processing the captured image grabbed by the second image capture device.

Next, explanation is given of the fact that the defect inspecting apparatus in accordance with the present invention can inspect a defect in the thread bottom face inspection zone with high accuracy. The defect inspecting apparatus in accordance with the present invention includes the third light source and the third image capture device. The third light source illuminates the thread bottom face inspection zone. The illumination of the thread bottom face inspection zone provided by the third light source has two implications; the light emitted from the third light source is caused to enter the thread bottom face inspection zone without being reflected by any portion of the pipe or tube, and the light emitted from the third light source is caused to enter the thread bottom face inspection zone after being reflected by a portion (for example, the load face) of the pipe or tube.

For the third image capture device, the optical axis is adjusted so that the reflection light that is emitted from the third light source and reflected by the thread bottom face inspection zone to the direction inclined through the angle C satisfying formula (3) inwardly in the pipe or tube axis direction relative to the vertical plane can be received. As described above, the load face is inclined through b° inwardly in the pipe or tube axis direction relative to the vertical plane. Therefore, if the reflection direction of the reflection light reflected by the boundary part between the load face and the thread bottom face is a direction inclined through b° or an angle smaller than b° inwardly in the pipe or tube axis direction relative to the vertical plane, the reflection light enters the load face. Also, if the reflection direction of the reflection light reflected by the inside end part in the pipe or tube axis direction of the thread bottom face inspection zone is a direction inclined through an angle larger than d° inwardly in the pipe or tube axis direction relative to the vertical plane, the reflection light enters the insertion face connecting with the inside end part in the pipe or tube axis direction of the thread bottom face. Therefore, the third image capture device the optical axis of which is adjusted so as to be capable of receiving the reflection light reflected by the thread bottom face inspection zone to the direction inclined through the angle C satisfying formula (3) inwardly in the pipe or tube axis direction relative to the vertical plane can receive the reflection lights reflected by the positions of the thread bottom face inspection zone, and therefore can grab the image of the thread bottom face inspection zone. Since the third image capture device can grab the image of the thread bottom face inspection zone in this manner, the defect inspecting apparatus in accordance with the present invention can inspect a defect in the thread bottom face inspection zone with high accuracy by processing the captured image grabbed by the third image capture device.

Also, the first image capture device is attached to the first light source so that the optical axis of the first image capture device is coaxial with the optical axis of the first light source. For this reason, the optical axis of the first light source can be adjusted so as to be inclined through the angle A outwardly in the pipe or tube axis direction relative to the vertical plane while the state in which the optical axis of the first image capture device is coaxial with the optical axis of the first light source is maintained. Therefore, in the defect inspecting apparatus in accordance with the present invention, by the adjustment of the optical axis of the first light source, a fear that the optical axis of the first image capture device may become non-coaxial with the optical axis of the first light source is eliminated, so that the adjustment for making the optical axis of the first image capture device coaxial with the optical axis of the first light source is unnecessary.

A preferred configuration of the defect inspecting apparatus in accordance with the present invention may include a configuration that includes a single light source member used as both of the second light source and the third light source; a single image capture device used as both of the second image capture device and the third image capture device; and a mirror the orientation of which can be changed over between an orientation at which the light emitted from the light source member is caused to enter the load face and the reflection light emitted from the light source member and reflected by the load face is received by the image capture device and an orientation at which the light emitted from the light source member is caused to enter the thread bottom face inspection zone and the reflection light emitted from the light source member and reflected by the thread bottom face inspection zone is received by the image capture device.

In this preferred configuration, when the mirror assumes the orientation at which the light emitted from the light source member is caused to enter the load face and the reflection light emitted from the light source member and reflected by the load face is received by the image capture device, the light source member functions as the second light source, and the image capture device functions as the second image capture device. Also, when the mirror assumes the orientation at which the light emitted from the light source member is caused to enter the thread bottom face inspection zone and the reflection light emitted from the light source member and reflected by the thread bottom face inspection zone is received by the image capture device, the light source member functions as the third light source, and the image capture device functions as the third image capture device.

According to this preferred configuration, since the single light source member is used as both of the second light source and the third light source as described above, the defect inspecting apparatus in accordance with the present invention need not be provided with two light sources (the second light source and the third light source) independently and separately. Similarly, since the single image capture device is used as both of the second image capture device and the third image capture device, the defect inspecting apparatus in accordance with the present invention need not be provided with two image capture devices (the second image capture device and the third image capture device) independently and separately. For this reason, according to the above-described preferred configuration, the number of parts of the defect inspecting apparatus in accordance with the present invention can be reduced.

A preferred configuration of the defect inspecting apparatus in accordance with the present invention may include a configuration in which the first image capture device is provided with a telecentric lens for receiving the reflection light reflected by the outer peripheral surface of the lip part, the second image capture device is provided with a telecentric lens for receiving the reflection light reflected by the load face, and the third image capture device is provided with a telecentric lens for receiving the reflection light reflected by the thread bottom face inspection zone.

Since the first to third image capture devices each are provided with a telecentric lens, even if the distances between the first to third image capture devices and the outer peripheral surface of the lip part, the load face, and the thread bottom face inspection zone, respectively, vary, distortion can be reduced from occurring in the captured images grabbed by the first to third image capture devices. Therefore, according to the above-described preferred configuration, even if the distances between the first to third image capture devices and the outer peripheral surface of the lip part, the load face, and the thread bottom face inspection zone, respectively, vary, defects on the outer peripheral surface of the lip part, on the load face, and in the thread bottom face inspection zone can be inspected.

A specific configuration of the defect inspecting apparatus in accordance with the present invention may include a configuration in which the first light source is a ring-shaped illuminator attached around the first image capture device, the second light source is a ring-shaped illuminator that has an optical axis coaxial with the optical axis of the second image capture device and is attached around the second image capture device, and the third light source is a ring-shaped illuminator that has an optical axis coaxial with the optical axis of the third image capture device and is attached around the third image capture device.

Also, the present invention provides a defect inspecting apparatus including a fourth light source in place of the second light source and the third light source; and a fourth image capture device in place of the second image capture device and the third image capture device, wherein the fourth light source illuminates the load face and the thread bottom face inspection zone; and the fourth image capture device is attached to the fourth light source, and has the optical axis adjusted so that the reflection light that is emitted from the fourth light source and reflected by the load face to the direction inclined through the angle C satisfying formula (3) inwardly in the pipe or tube axis direction relative to the vertical plane and the reflection light that is emitted from the fourth light source and reflected by the thread bottom face inspection zone to the direction inclined through the angle C satisfying formula (3) inwardly in the pipe or tube axis direction relative to the vertical plane can be received, and the reflection lights are received to grab the images of the load face and the thread bottom face inspection zone; and the inspection device inspects defects on the outer peripheral surface of the lip part, on the load face, and in the thread bottom face inspection zone by processing the captured images grabbed by the first and fourth image capture devices in place of the captured images grabbed by the first to third image capture devices:

$$b < C \leq d \qquad (3)$$

$b°$ being an angle (smaller than 90°) formed between the load face and the vertical plane in the cross section of the pipe or tube including the pipe or tube axis; and $d°$ being an angle (smaller than 90°) formed between a straight line and the vertical plane in the cross section of the pipe or tube including the pipe or tube axis, the straight line connecting a rear end part of the thread bottom face inspection zone on the thread bottom face to the front end part of the insertion face of the external thread part, the insertion face connecting with an inside end part in the pipe or tube axis direction of the thread bottom face.

Like the above-described defect inspecting apparatus including the second light source, the third light source, the second image capture device, and the third image capture device (hereinafter, referred to as "the second light source and the like"), the defect inspecting apparatus including the fourth light source and the fourth image capture device inspects defects on the outer peripheral surface of the lip part, on the load face, and in the thread bottom face inspection zone by processing the captured images of the outer peripheral surface of the lip part, the load face, and the thread bottom face inspection zone. In the defect inspecting apparatus including the fourth light source and the fourth image capture device, the image of the outer peripheral surface of the lip part is grabbed by the first image capture device like the defect inspecting apparatus including the second light source and the like. In the defect inspecting apparatus including the fourth light source and the fourth image capture device, the images of the load face and the thread bottom face inspection zone are grabbed by the fourth light source and the fourth image capture device.

As described above, in the defect inspecting apparatus including the second light source and the like, to cause the second image capture device for grabbing the image of the load face to receive the reflection light reflected by the load face, the optical axis is adjusted so that the reflection light reflected to the direction inclined through the angle B inwardly in the pipe or tube axis direction relative to the vertical plane can be received. The lower limits of the angle B and the angle C are equal to each other, being $b°$, but the upper limit $d°$ of the angle C is smaller than the upper limit $c°$ of the angle B. Therefore, the range of the angle C is included in the range of the angle B. For this reason, the fourth image capture device the optical axis of which is adjusted so as to be capable of receiving the reflection lights reflected by the load face and the thread bottom face inspection zone to the direction inclined through the angle C inwardly in the pipe or tube axis direction relative to the vertical plane can simultaneously receive the reflection lights reflected by respective positions of the load face and the thread bottom face inspection zone. For the fourth image capture device, by simultaneously receiving the reflection lights reflected by respective positions of the load face and the thread bottom face inspection zone, the images of both the load face and the thread bottom face inspection zone can be grabbed by one image capture process. Therefore, according to the defect inspecting apparatus including the fourth image capture device, defects on the load face and in the thread bottom face inspection zone can be inspected by a small number of image captures, and the inspection time of the load face and in the thread bottom face inspection zone can be shortened.

The illumination of the load face and the thread bottom face inspection zone provided by the fourth light source implies that the light emitted from the fourth light source is caused to enter the load face and the thread bottom face inspection zone without being reflected by any portion of the pipe or tube.

A preferred configuration of the defect inspecting apparatus in accordance with the present invention including the fourth light source and the fourth image capture device may include a configuration in which the first image capture device is provided with a telecentric lens for receiving the reflection light reflected by the outer peripheral surface of the lip part, and the fourth image capture device is provided with a telecentric lens for receiving the reflection light reflected by the load face and the reflection light reflected by the thread bottom face inspection zone.

Since the first and fourth image capture devices each are provided with a telecentric lens, even if the distances between the first and fourth image capture devices and the outer peripheral surface of the lip part, and the load face and the thread bottom face inspection zone, respectively, vary, distortion can be restrained from occurring in the captured images grabbed by the first and fourth image capture devices. Therefore, according to the above-described preferred configuration, even if the distances between the first and fourth image capture devices and the outer peripheral surface of the lip part, and the load face and the thread bottom face inspection zone, respectively, vary, defects on the outer peripheral surface of the lip part, on the load face, and in the thread bottom face inspection zone can be inspected.

A specific configuration of the defect inspecting apparatus in accordance with the present invention including the fourth light source and the fourth image capture device may include a configuration in which the first light source is a ring-shaped illuminator attached around the first image capture device, and the fourth light source is a ring-shaped illuminator that has an optical axis coaxial with the optical axis of the fourth image capture device and is attached around the fourth image capture device.

Advantageous Effects of Invention

The present invention can provide the defect inspecting apparatus capable of inspecting defects with high accuracy on the load face and in the thread bottom face inspection zone of a pipe or tube in which the load face is inclined inwardly in the pipe or tube axis direction, and also capable of inspecting a defect on the outer peripheral surface of the lip part.

BRIEF DESCRIPTION OF DRAWINGS

FIG. 5 is a schematic view of an image processing filter.

FIG. 7 is a schematic view of a captured image grabbed by an image capture device shown in FIG. 1.

DESCRIPTION OF EMBODIMENTS

First Embodiment

Figure 1:
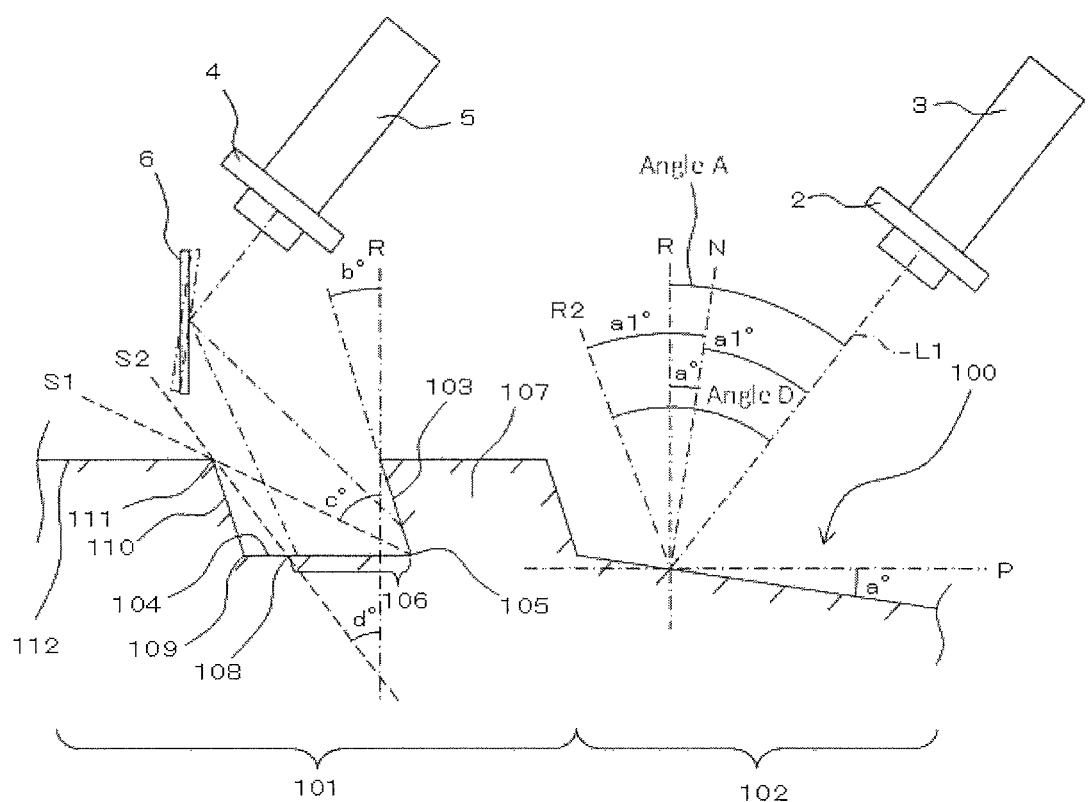
FIG. 1 is a view showing a schematic configuration of a defect inspecting apparatus of a first embodiment of the present invention, showing a cross section including the inspected pipe axis.

Hereunder, the defect inspection carried out by a defect inspecting apparatus of a first embodiment is explained. FIG. 1 is a view showing a schematic configuration of the defect inspecting apparatus of the first embodiment, showing a cross section including the inspected pipe axis. In this embodiment, the inspected pipe is an oil well steel pipe 100.

As shown in FIG. 1, in the end portion of the oil well steel pipe 100, an external thread part 101 and a lip part 102 are provided in that order from the inside (the left-hand side in FIG. 1) in the pipe axis direction P. In a cross section including the pipe axis of the oil well steel pipe 100, a load face 103 of the external thread part 101 is inclined through b° inwardly (to the counterclockwise direction in FIG. 1) in the pipe axis direction P relative to the vertical plane R perpendicular to the pipe axis direction P. The load face 103 is a side face on the inside in the pipe axis direction P of the side faces of a thread ridge part 107. The lip part 102 is tapered such that the dimension in the direction perpendicular to the pipe axis direction P decreases outwardly (to the right-hand side in FIG. 1) in the pipe axis direction P. In the cross section including the pipe axis of the oil well steel pipe 100, the outer peripheral surface of the lip part 102 makes an angle of a° relative to the pipe axis direction P.

The defect inspecting apparatus of this embodiment includes a first light source 2, a first image capture device 3, a single light source member 4, a single image capture device 5, a mirror 6, and an inspection device (not shown). The first light source 2 illuminates the outer peripheral surface of the lip part 102 so that the optical axis L1 is inclined through an angle A satisfying formula (1) described below outwardly (to the clockwise direction in FIG. 1) in the pipe axis direction P relative to the vertical plane R. The first light source 2 is a ring-shaped illuminator attached around the first image capture device 3.

$$a-45 \leq A \leq a+45 \qquad (1)$$

The first image capture device 3 takes the image of the outer peripheral surface of the lip part 102 by receiving the reflection light emitted from the first light source 2 and reflected by the outer peripheral surface of the lip part 102. The optical axes of the first light source 2 and the first image capture device 3 are coaxial. In this embodiment, the first image capture device 3 is provided with a telecentric lens as a lens for receiving the reflection light reflected by the outer peripheral surface of the lip part 102.

As described above, the optical axis L1 of the first light source 2 illuminating the outer peripheral surface of the lip part 102 is inclined through the angle A outwardly in the pipe axis direction P relative to the vertical plane R. In other words, the light emitted from the first light source 2 enters the outer peripheral surface of the lip part 102 from the direction inclined through a1°, which is not larger than 45°, relative to the normal direction N of the outer peripheral surface of the lip part 102. Therefore, an angle D formed between the direction from which the light emitted from the first light source 2 enters the outer peripheral surface of the lip part 102 (the direction of the optical axis L1 of the first light source 2) and the specular direction R2 in which the light emitted from the first light source 2 and entering the outer peripheral surface of the lip part 102 is specularly reflected by the outer peripheral surface of the lip part 102 so that the angle of incidence and the angle of reflection are equal to each other is 90° at the maximum. Since the optical axis of the first image capture device 3 is coaxial with the optical axis L1 of the first light source 2, the direction of the optical axis of the first image capture device 3 coincides with the direction from which the light emitted from the first light source 2 enters the outer peripheral surface of the lip part 102. Therefore, the angle formed between the direction of the optical axis of the first image capture device 3 and the aforementioned specular direction R2 is not larger than 90°. The quantity of light entering the outer peripheral surface of the lip part 102 and reflected by the outer peripheral surface thereof tends to increase as the reflection direction is closer to the direction such that the angle of incidence and the angle of reflection relative to the outer peripheral surface of the lip part 102 are equal to each other. Therefore, the first image capture device 3 such that the angle formed between the aforementioned specular direction R2 and the direction of optical axis is not larger than 90° can receive the reflection light, which is emitted from the first light source 2 and reflected by the outer peripheral surface of the lip part 102, in large amounts, so that the image of the outer peripheral surface of the lip part 102 can be grabbed clearly.

The light source member 4 is used as both of a second light source and a third light source. The second light source is a light source for illuminating the load face 103. The third light source is a light source for illuminating a thread bottom face inspection zone 106. The thread bottom face inspection zone 106 is a zone of a thread bottom face 104 ranging from a boundary part 105 between the load face 103 and the thread bottom face 104 to a portion 108 of the thread bottom face 104 spaced apart inwardly by a predetermined distance from the boundary part 105 in the pipe axis direction. The light emitted from the light source member 4 is reflected by the mirror 6, and then enters the load face 103 or the thread bottom face inspection zone 106. The orientation of the mirror 6 can be changed. By changing the orientation of the mirror 6, the incident destination of light emitted from the light source member 4 can be changed over between the load face 103 and the thread bottom face inspection zone 106. Therefore, by changing the orientation of the mirror 6, the light source member 4 is changed over between a state of functioning as the second light source and a state of functioning as the third light source. In this embodiment, the light source member 4 is a ring-shaped illuminator attached around the image capture device 5.

The image capture device 5 is used as both of a second image capture device and a third image capture device. The second image capture device is an image capture device that is attached to the second light source, and has the optical axis adjusted so that the reflection light that is emitted from the second light source and reflected by the load face 103 to the direction inclined through an angle B satisfying formula (2) inwardly in the pipe axis direction P relative to the vertical plane R can be received, and the reflection light is received to grab the image of the load face 103.

$$b < B \leq c \quad (2)$$

c° is an angle (smaller than 90°) formed between a straight line S1 and the vertical plane R as shown in FIG. 1. The straight line S1 is connecting, in the cross section including the pipe axis, the above-described boundary part 105 to a front end part 111 of an insertion face 110 of the external thread part 101, the insertion face 110 connecting with an inside end part 109 in the pipe axis direction of the thread bottom face 104. The insertion face 110 is a side face on the outside in the pipe axis direction P of the side faces of the thread ridge part 107. The front end part 111 of the insertion face 110 is a boundary part between the insertion face 110 and a thread top face 112 of the thread ridge part 107.

The third image capture device is an image capture device that is attached to the third light source, and has the optical axis adjusted so that the reflection light that is emitted from the third light source and reflected by the thread bottom face inspection zone 106 to the direction inclined through an angle C satisfying formula (3) inwardly in the pipe axis direction P relative to the vertical plane R can be received, and the reflection light is received to grab the image of the thread bottom face inspection zone 106.

$$b < C \leq d \quad (3)$$

d° is an angle (smaller than 90°) formed between a straight line S2 and the vertical plane R as shown in FIG. 1. The straight line S2 is connecting, in the cross section including the pipe axis, an inside end part 108 in the pipe axis direction P of the thread bottom face inspection zone 106 to the front end part 111 of the insertion face 110.

As shown in FIG. 1, the image capture device 5 receives the reflection light reflected by the load face 103 or the thread bottom face inspection zone 106 via the mirror 6. By changing the orientation of the mirror 6, the reflection light received by the image capture device 5 can be changed over between the reflection light reflected by the load face 103 and the reflection light reflected by the thread bottom face inspection zone 106. That is, by changing the orientation of the mirror 6, the image capture device 5 can be changed over between a state of functioning as the second image capture device and a state of functioning as the third image capture device. In this embodiment, the optical axes of the light source member 4 and the image capture device 5 are coaxial, and these optical axes are inclined outwardly in the pipe axis direction P relative to the vertical plane R. Also, in this embodiment, the image capture device 5 is provided with a telecentric lens as a lens for receiving the reflection light reflected by the load face 103 and the reflection light reflected by the thread bottom face inspection zone 106.

The mirror 6 is turnable around an axis intersecting at right angles with the pipe axis direction (intersecting at right angles with the paper surface of FIG. 1). The orientation of the mirror 6 can be changed over between an orientation for causing the light emitted from the light source member 4 to enter the load face 103 and for causing the image capture device 5 to receive the reflection light reflected by the load face 103 to the direction inclined through the angle B inwardly in the pipe axis direction P relative to the vertical plane R (hereinafter, referred to as a "first orientation") and an orientation for causing the light emitted from the light source member 4 to enter the thread bottom face inspection zone 106 and for causing the image capture device 5 to receive the reflection light reflected by the thread bottom face inspection zone 106 to the direction inclined through the angle C inwardly in the pipe axis direction P relative to the vertical plane R (hereinafter, referred to as a "second orientation"). At the first orientation, the mirror 6 is inclined through an angle E satisfying formula (4) outwardly in the pipe axis direction P relative to the vertical plane R.

$$r1 > E \geq r2 \tag{4}$$

Figure 2A:
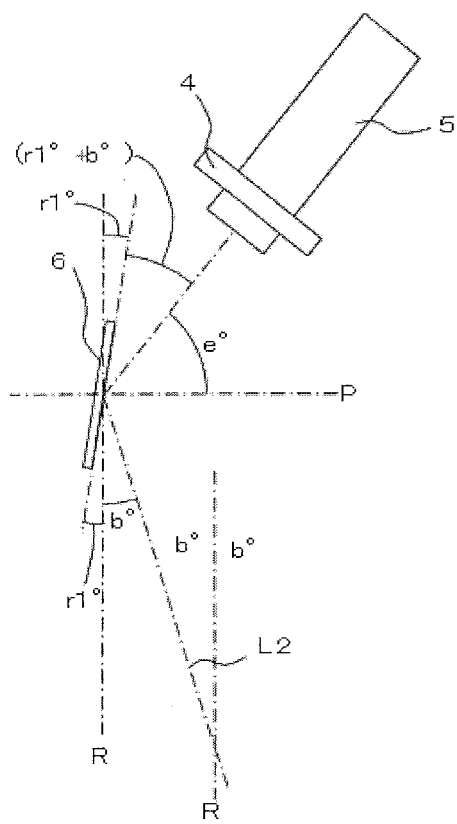
FIG. 2A is a schematic view showing the orientation of a mirror shown in FIG. 1 in the case where the light entering the mirror from the direction inclined through b° inwardly in the pipe axis direction relative to the vertical plane perpendicular to the pipe axis enters an image capture device.
Figure 2B:
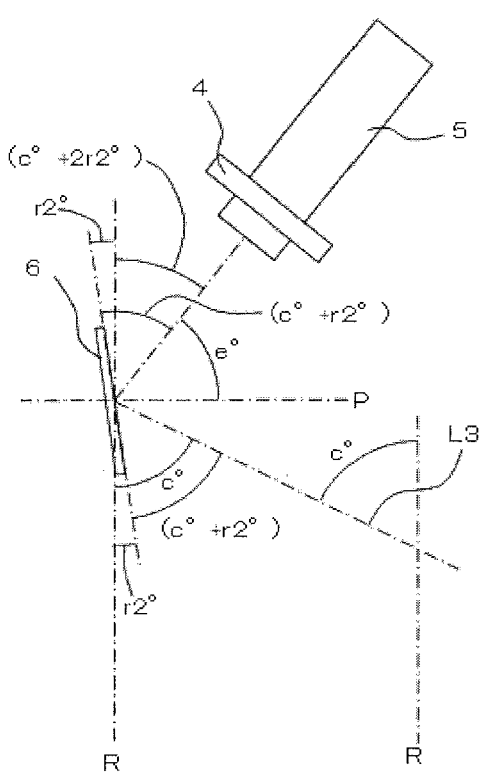
FIG. 2B is a schematic view showing the orientation of the mirror in the case where the light entering the mirror from the direction inclined through c° inwardly in the pipe axis direction relative to the vertical plane perpendicular to the pipe axis enters the image capture device.

As shown in FIGS. 2A and 2B, r1° and r2° are angles representing the degree of outward inclination of the mirror 6 in the pipe axis direction P relative to the vertical plane R. In the state shown in FIG. 2B, since the mirror 6 is inclined inwardly in the pipe axis direction P relative to the vertical plane R, r2° is a negative angle.

As shown in FIG. 2A, when the angle E is r1°, light L2 entering the mirror 6 from the direction inclined through b° inwardly in the pipe axis direction P relative to the vertical plane R enters the image capture device 5. From FIG. 2A, since 90°=r1°+(r1°+b°)+e°, formula (5) can be derived.

$$r1° = (90° - b° - e°)/2 \tag{5}$$

e° is an angle representing the degree of inward inclination of the optical axis of the image capture device 5 in the pipe axis direction P relative to the pipe axis direction P.

Also, as shown in FIG. 2B, when the angle E is r2°, light L3 entering the mirror 6 from the direction inclined through c° inwardly in the pipe axis direction P relative to the vertical plane R enters the image capture device 5. From FIG. 2B, since 90°=(c°+2r2°)+e°, formula (6) can be derived.

$$r2° = (90° - c° - e°)/2 \tag{6}$$

Because of the above description, at the first orientation, the light entering the mirror 6 from the direction inclined through b° or an angle smaller than b° inwardly in the pipe axis direction P relative to the vertical plane R and the light entering the mirror 6 from the direction inclined through an angle larger than c° inwardly in the pipe axis direction P relative to the vertical plane R are not received by the image capture device 5. On the other hand, the load face 103 is inclined through b° inwardly in the pipe axis direction P relative to the vertical plane R. Therefore, all of the reflection lights reflected by the load face 103 are reflected to the direction inclined through an angle larger than b° inwardly in the pipe axis direction relative to the vertical plane R. Also, if the reflection direction of the reflection light reflected by the above-described boundary part 105 is the direction inclined through an angle larger than c° inwardly in the pipe axis direction P relative to the vertical plane R, the reflection light enters the insertion face 110. Therefore, if the angle E satisfies formula (4), the image capture device 5 can receive the reflection light reflected by the load face 103, and can grab the image of the load face 103 by receiving the reflection light. That is, if the angle E satisfies formula (4), the image capture device 5 functions as the second image capture device.

On the other hand, at the second orientation, the mirror 6 is inclined through the angle E satisfying formula (7) outwardly in the pipe axis direction P relative to the vertical plane R.

$$r1° > E \leq r3° \tag{7}$$

Figure 3:
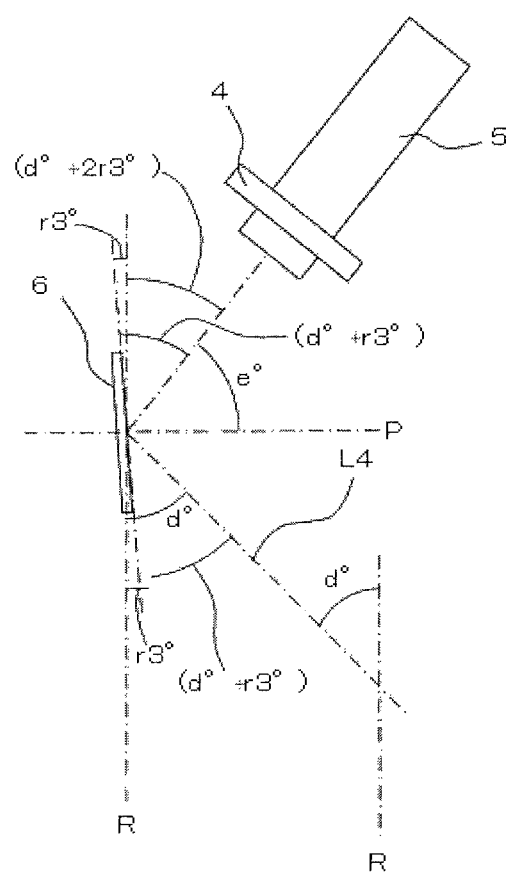
FIG. 3 is a schematic view showing the orientation of a mirror shown in FIG. 1 in the case where the light entering the mirror from the direction inclined through d° inwardly in the pipe axis direction relative to the vertical plane perpendicular to the pipe axis enters an image capture device.

As shown in FIG. 3, r3° is, like r1° and r2°, an angle representing the degree of outward inclination of the mirror 6 in the pipe axis direction P relative to the vertical plane R. In the state shown in FIG. 3, since the mirror 6 is inclined inwardly in the pipe axis direction P relative to the vertical plane R, r3° is a negative angle. When the angle E is r3°, light L4 entering the mirror 6 from the direction inclined through d° inwardly in the pipe axis direction P relative to the vertical plane R enters the image capture device 5. From FIG. 3, since 90°=(d°+2r3°)+e°, formula (8) can be derived.

$$r3° = (90° - d° - e°)/2 \tag{8}$$

Because of the above description, at the second orientation, the light entering the mirror 6 from the direction inclined through b° or an angle smaller than b° inwardly in the pipe axis direction P relative to the vertical plane R and the light entering the mirror 6 from the direction inclined through an angle larger than d° inwardly in the pipe axis direction P relative to the vertical plane R are not received by the image capture device 5. On the other hand, the load face 103 is inclined through the angle b° inwardly in the pipe axis direction P relative to the vertical plane R. Therefore, the reflection light reflected by the above-described boundary part 105 to the direction inclined through the angle b° or an angle smaller than b° inwardly in the pipe axis direction P relative to the vertical plane R enters the load face 103. Also, the reflection light reflected by the inside end part 108 in the pipe axis direction of the thread bottom face inspection zone 106 to the direction inclined through an angle larger than the angle d° inwardly in the pipe axis direction P relative to the vertical plane R enters the insertion face 110. Therefore, if the angle E satisfies formula (7), the image capture device 5 can receive the reflection light reflected by the thread bottom face inspection zone 106, and can grab the image of the thread bottom face inspection zone 106 by receiving the reflection light. That is, if the angle E satisfies formula (7), the image capture device 5 functions as the third image capture device.

The inspection device inspects defects on the outer peripheral surface of the lip part 102, on the load face 103, and in the thread bottom face inspection zone 106 by processing the captured image grabbed by the first image capture device 3 and the captured image grabbed by the image capture device 5. The image processing is performed as described below.

Figure 4:
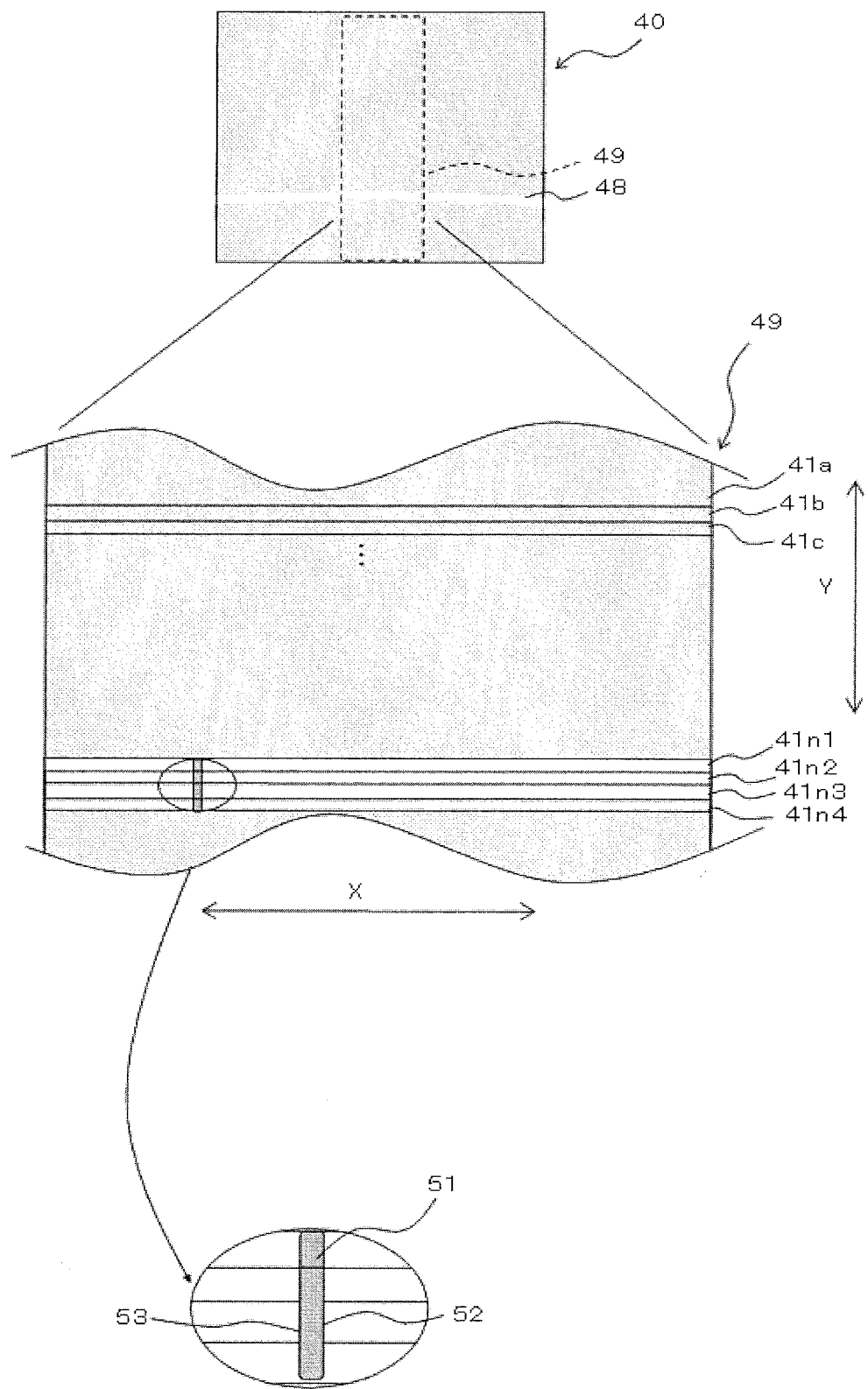
FIG. 4 is a schematic view of a captured image grabbed by a first image capture device shown in FIG. 1.

First, the image processing for inspecting a defect on the outer peripheral surface of the lip part 102 is explained. Hereunder, explanation is given of the case where the defect inspection is an inspection for checking whether or not a linear flaw extending in the pipe axis direction P is present on the outer peripheral surface of the lip part 102. FIG. 4 shows a captured image 40 grabbed by the first image capture device 3. In FIG. 4 and FIGS. 6 and 7, described later, the double-headed arrow-marked Y direction is the direction corresponding to the pipe axis direction P (hereinafter, the direction corresponding to the pipe axis direction P is referred to as the "Y direction"). Of the captured image 40, a region (white region) having a high brightness value extending in the direction perpendicular to the Y direction (hereinafter, the double-headed arrow-marked X direction, that is, the direction perpendicular to the Y direction in FIGS. 4, 6 and 7 is referred to as the "X direction") is a lip part region 48 corresponding to the outer peripheral surface of the lip part 102. The reason why the brightness value of the lip part region 48 is high is that the reflection light reflected by the outer peripheral surface of the lip part 102 is received by the first image capture device 3 in large amounts.

First, when the captured image 40 grabbed by the first image capture device 3 is entered, the inspection device extracts a ROI (region of the interest) 49 from the captured image 40. The ROI 49 is a portion in which the lip part region 48 is substantially parallel to the X direction. The positional information of the ROI 49 is calculated in advance from the position of the oil well steel pipe 100 with respect to the first image capture device 3 at the time of image capture, the outside diameter of the oil well steel pipe 100, and the like, and is stored in the inspection device in advance. After extracting the ROI 49, the inspection device performs preprocessing such as noise cancellation on the region 49.

Next, the inspection device identifies pixel lines constituting the lip part region 48 from among the pixel lines 41a, 41b, 41c . . . extending in the X direction in the ROI 49. The identification is made as described below. First, the inspection device calculates the sum of the brightness values of all pixels constituting the pixel lines 41a, 41b, 41c . . . for each pixel line. The inspection device identifies pixel lines in which the sum of the calculated brightness values is larger than a predetermined threshold value as the pixel lines constituting the lip part region 48. In this embodiment, pixel lines 41n1, 41n2, 41n3 and 41n4 are identified as the pixel lines constituting the lip part region 48. When the pixel lines constituting the lip part region 48 cannot be identified, the inspection device finishes the image processing for defect inspection at that time.

Figure 5:
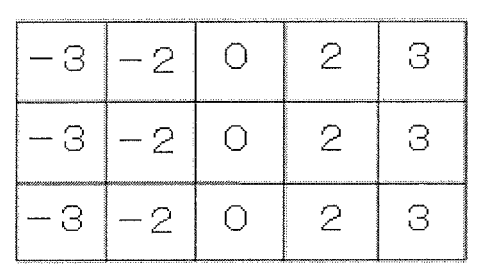

Next, from among all the pixels constituting one pixel line identified as the pixel lines constituting the lip part region 48, the inspection device detects a candidate of pixel constituting one-side edge 52 (hereinafter, referred to as "one-side edge candidate pixel") and a candidate of pixel constituting the other-side edge 53 (hereinafter, referred to as "the other-side edge candidate pixel") of a linear flaw region 51 corresponding to a linear flaw. The one-side and the other-side edge candidate pixels are detected as described below. The inspection device identifies the pixel that is positioned in a region in which the brightness value increases steeply toward one side (right side in the embodiment) in the X direction as one-side edge candidate pixel, and identifies the pixel that is positioned in a region in which the brightness value decreases steeply toward one side in the X direction as the other-side edge candidate pixel. The reason why the one-side and the other-side edge candidate pixels are identified in this manner is that the pixel constituting the linear flaw region 51 has a smaller brightness value than the pixels constituting other regions of the pixel line corresponding to the outer peripheral surface of the lip part 102. This is because in a portion where a linear flaw occurs of the outer peripheral surface of the lip part 102, the orientation of that portion is changed by the occurrence of linear flaw, and the reflection light reflected by that portion becomes less liable to be received by the first image capture device 3. In this embodiment, the inspection device calculates the degree of steep change of the brightness value toward one side in the X direction by using an image processing filter shown in FIG. 5. In this manner, the inspection device detects the one-side edge candidate pixel and the other-side edge candidate pixel from among all the pixels constituting all the pixel lines identified as the pixel lines constituting the lip part region 48. When the one-side and other-side edge candidate pixels cannot be detected, the inspection device finishes the image processing for defect inspection at that time.

When the one-side and other-side edge candidate pixels are detected, the inspection device performs labeling processing on the one-side edge candidate pixel, and thereby detects a candidate of pixel group constituting the one-side edge 52 of the linear flaw region 51 (hereinafter, referred to as "one-side edge candidate pixel group"). Similarly, the inspection device performs labeling processing on the other-side edge candidate pixel, and thereby detects a candidate of pixel group constituting the other-side edge 53 of the linear flaw region 51 (hereinafter, referred to as "the other-side edge candidate pixel group").

Next, based on the length in the Y direction and the orientation in the longitudinal direction of each of the one-side and other-side edge candidate pixel groups, the space between the one-side edge candidate pixel group and other-side edge candidate pixel group, and the like, the inspection device determines whether or not each of the one-side and other-side edge candidate pixel groups is a pixel group actually constituting the one-side edge 52 and the other-side edge 53 of the linear flaw region 51. If it is determined that each of the one-side and other-side edge candidate pixel groups is a pixel group actually constituting the one-side and the other-side edges 52 and 53 of the linear flaw region 51, the inspection device determines that a linear flaw occurs in a portion on the outer peripheral surface of the lip part 102 corresponding to the one-side and the other-side edge candidate pixel groups. When the captured image 40 is displayed on a monitor, the inspection device processes the captured image 40 so that the one-side and the other-side edge candidate pixel groups are surrounded by a red frame or the like. By this processing of the captured image 40, the operator can decide whether or not a linear flaw has occurred on the outer peripheral surface of the lip part 102 and can determine the portion in which the linear flaw has occurred by looking at the monitor on which the captured image 40 is displayed.

Figure 6A:
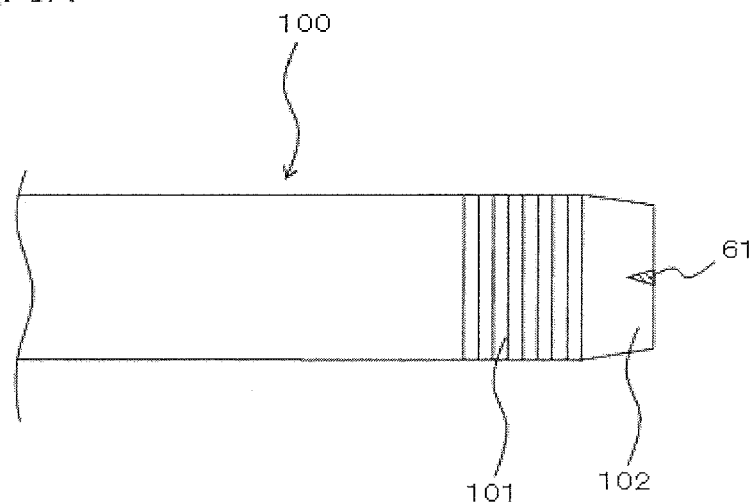
FIGS. 6A and 6B are schematic views of a captured image grabbed by a first image capture device shown in FIG. 1.
Figure 6B:
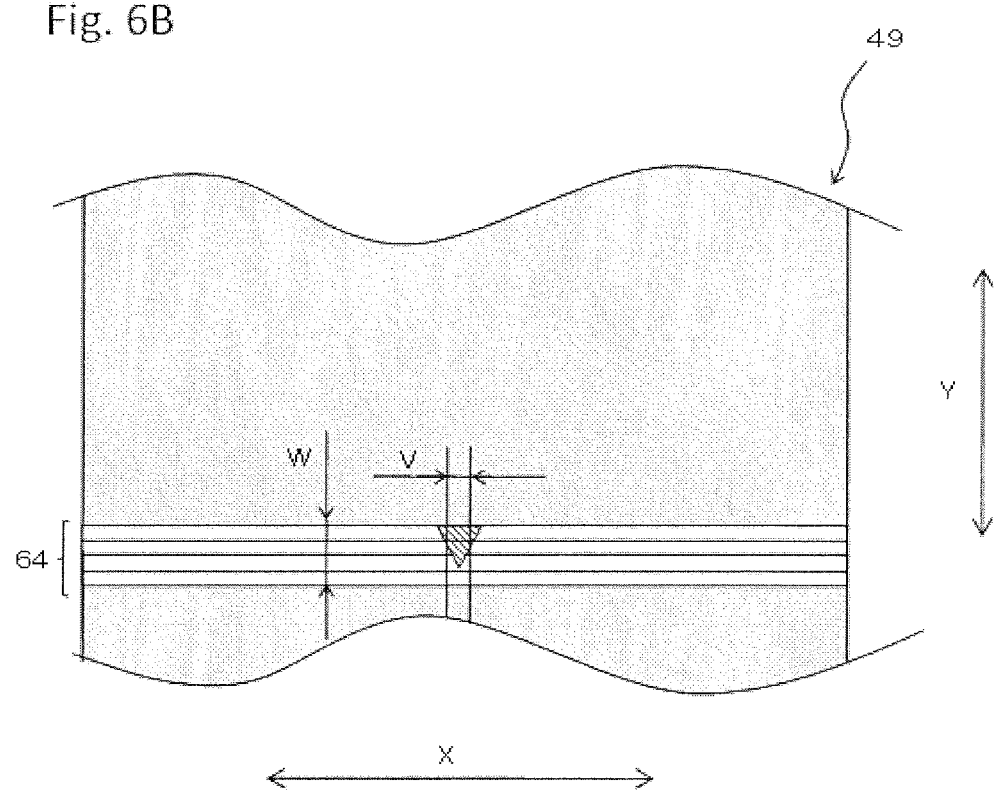

Hereunder, explanation is given of the case where inspection is carried out to check whether or not, as shown in FIG. 6A, a flaw 61 extending from the end portion in the pipe axis direction P to the center side on the outer peripheral surface of the lip part 102 is present on the outer peripheral surface of the lip part 102. As shown in FIG. 6B, the inspection device identifies the pixel lines constituting the lip part region 48. The inspection device calculates an average W1 of lengths W in the Y direction of a region 64 consisting of all pixel lines identified as the pixel lines constituting the lip part region 48. The length W in the Y direction of the region 64 is a length in the Y direction of a pixel group consisting of pixels the brightness values of which are larger than the predetermined threshold value. Next, in the case where, in the region 64, a section V in which the length W in the Y direction is shorter than the average W1 by a predetermined length or more continues longer than the predetermined pixels in the X direction, the inspection device determines that the flaw 61 has occurred in this section. Then, the inspection device processes the captured image so that the section is highlighted when the captured image 40 is displayed on the monitor.

Next, the image processing for defect inspection of the load face 103 is explained. FIG. 7 shows a captured image 70 grabbed by the image capture device 5 (that is, the second image capture device) when the mirror 6 assumes the first orientation. In the captured image 70, a region in which the brightness value is the lowest, a region in which it is the second lowest, and a region in which it is the highest are present. The region of the lowest brightness value is a load face region 71 corresponding to the load face 103. The region of the second lowest brightness value is a region corresponding to the thread bottom face inspection zone 106 (hereinafter, referred to as a "thread bottom face region 72"). The region of the highest brightness value is a thread top face region 73 corresponding to the thread top face 112. Although the thread bottom face inspection zone 106 and the thread top face 112 are substantially parallel to each other, the thread bottom face region 72 has a brightness value lower than that of the thread top face region 73 because some light reflected by the thread bottom face inspection zone 106 enters the load face 103 and the insertion face 110 and does not enter the image capture device 5.

When the captured image 70 is entered, the inspection device extracts a ROI (region of the interest) 74 from the captured image 70. The ROI 74 is a portion in which the load face region 71, the thread bottom face region 72, and the thread top face region 73 are substantially parallel to the X direction. The positional information of the ROI 74 is calculated in advance from the position of the oil well steel pipe 100 with respect to the image capture device 5 at the time of image capture, the outside diameter of the oil well steel pipe 100, and the like, and is stored in the inspection device in advance. After extracting the ROI 74, the inspection device performs preprocessing such as noise reduction on the region.

Next, the inspection device identifies pixel lines constituting the load face region 71 from among the pixel lines 75a, 75b, 75c . . . of the captured image 70 extending in the X direction in the ROI 74. The identification is made as described below. First, the inspection device calculates the sum of the brightness values of all pixels constituting the pixel lines 75a, 75b, 75c . . . for each pixel line. The inspection device identifies pixel lines in which the sum of the calculated brightness values is smaller than the predetermined threshold value as the pixel lines constituting the load face region 71. When the pixel lines constituting the load face region 71 cannot be identified, the inspection device finishes the image processing for defect inspection at that time.

Figure 8:
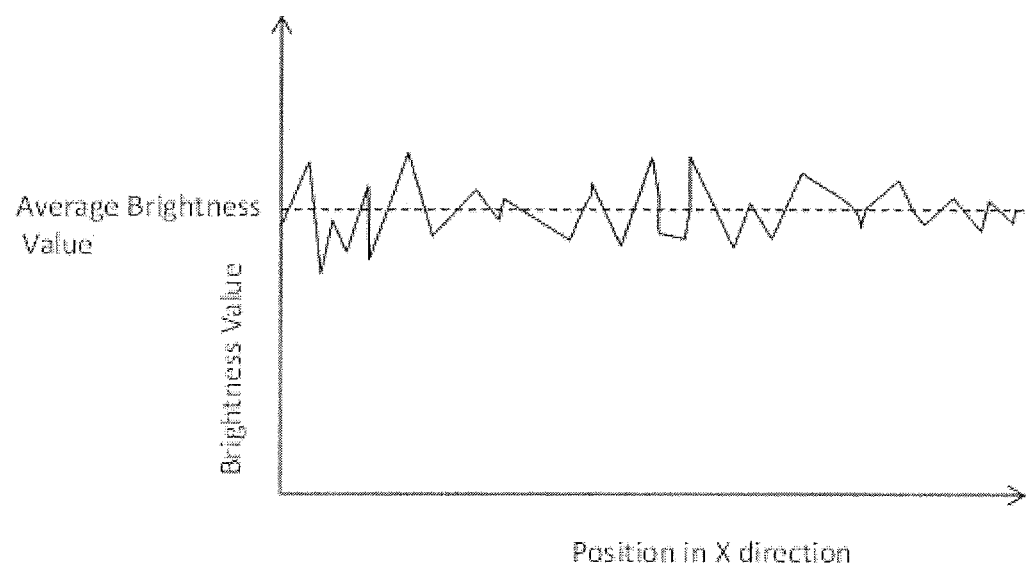
FIG. 8 is a graph showing the distribution of a brightness value in the X direction of a pixel line.

Next, the inspection device calculates a brightness value line (refer to FIG. 8) showing the distribution in the X direction of the brightness values of one pixel line (hereinafter, referred to a "remarked pixel line") of the pixel lines identified as the pixel lines constituting the load face region 71, and the average of brightness values (average brightness value) of the pixels constituting that pixel line. The inspection device determines whether or not the number of intersections of the brightness value line with the average brightness value is not smaller than a predetermined threshold value, and the average brightness value is smaller than a predetermined threshold value. If it is determined that the number of intersections is not smaller than the predetermined threshold value, and the average brightness value is smaller than the predetermined threshold value, the inspection device determines that a flaw has occurred in a portion of the load face 103 corresponding to the remarked pixel line. On the other hand, if it is determined that the number of intersections is not smaller than the predetermined threshold value, and the average brightness value exceeds the predetermined threshold value, the inspection device determines that no flaw has occurred in the portion of the load face 103 corresponding to the remarked pixel line. Similarly, the inspection device determines whether or not a flaw has occurred in portions corresponding to all the pixel lines identified as the pixel lines constituting the load face region 71. When the captured image 70 is displayed on the monitor, the inspection device processes the captured image 70 so that the pixel line corresponding to the portion of the load face 103 determined that a flaw has occurred therein is surrounded by a red frame or the like. By the display of the captured image 70 thus processed on the monitor, the operator can decide whether or not a flaw has occurred on the load face 103 and can determine the portion in which the flaw has occurred by looking at the monitor.

Next, the image processing for defect inspection of the thread bottom face inspection zone 106 is explained. The image processing for defect inspection of the thread bottom face inspection zone 106 is performed on the captured image grabbed by the image capture device 5 (that is, the third image capture device) when the mirror 6 assumes the second orientation. In the captured image at the time when the mirror 6 assumes the second orientation, like the captured image 70 shown in FIG. 7, the load face region 71, the thread bottom face region 72, and the thread top face region 73 are present. Herein, the image processing for defect inspection of the thread bottom face inspection zone 106 is explained assuming that the captured image 70 shown in FIG. 7 is a captured image grabbed by the image capture device 5 when the mirror 6 assumes the second orientation.

When the captured image 70 is entered, the inspection device extracts the ROI 74 from the captured image 70.

Next, the inspection device identifies pixel lines constituting the load face region 71 from among the pixel lines 75a, 75b, 75c . . . of the captured image 70 extending in the X direction in the ROI 74. The identification is made by the same method as the method used in the image processing for defect inspection of the load face 103. Next, the inspection device identifies pixel lines constituting the thread top face region 73 from among the pixel lines 75a, 75b, 75c . . . . The identification is made as described below. First, the inspection device calculates the sum of the brightness values of all pixels constituting the pixel lines 75a, 75b, 75c . . . for each pixel line. The inspection device identifies pixel lines in which the sum of the calculated brightness values is not smaller than the predetermined threshold value as the pixel lines constituting the thread top face region 73. Next, the inspection device identifies the load face region 71 from the pixel lines constituting the load face region 71, and identifies the thread top face region 73 from the pixel lines constituting the thread top face region 73. Next, the inspection device identifies a region between the load face region 71 and the thread top face region 73 as the thread bottom face region 72. When the pixel lines constituting the load face region 71 and the thread top face region 73 cannot be identified, the inspection device finishes the image processing for defect inspection at that time.

Next, the inspection device calculates a brightness value line showing the distribution in the X direction of the brightness values of one pixel line (hereinafter, referred to a "remarked pixel line") of the pixel lines constituting the thread bottom face region 72, and the average of brightness values (average brightness value) of the pixels constituting that pixel line. The inspection device determines whether or not the number of intersections of the brightness value line with the average brightness value is not smaller than the predetermined threshold value, and the average brightness value is smaller than the predetermined threshold value. If it is determined that the number of intersections is not smaller than the predetermined threshold value, and the average brightness value is smaller than the predetermined threshold value, the inspection device determines that a flaw has occurred in a portion of the thread bottom face inspection zone 106 corresponding to the remarked pixel line. On the other hand, if it is determined that the number of intersections is not smaller than the predetermined threshold value, and the average brightness value exceeds the predetermined threshold value, the inspection device determines that no flaw has occurred in the portion of the thread bottom face inspection zone 106 corresponding to the remarked pixel line. Similarly, the inspection device determines whether or not a flaw has occurred in portions corresponding to all the pixel lines constituting the thread bottom face region 72. When the captured image 70 is displayed on the monitor, the inspection device processes the captured image 70 so that the pixel line corresponding to the portion of the thread bottom face inspection zone 106 determined that a flaw has occurred therein is surrounded by a red frame or the like. By the display of the captured image 70 thus processed on the monitor, the operator can decide whether or not a flaw has occurred on the thread bottom face inspection zone 106 and can determine the portion in which the flaw has occurred by looking at the monitor.

As described above, according to the defect inspecting apparatus of this embodiment, defects occurring on the outer peripheral surface of the lip part 102, on the load face 103, and in the thread bottom face inspection zone 106 can be inspected.

The first image capture device 3 is attached to the first light source 2 so that the optical axis of the first image capture device 3 is coaxial with the optical axis L1 of the first light source 2. For this reason, the optical axis of the first light source 2 can be adjusted so as to be inclined through the angle A outwardly in the pipe axis direction P relative to the vertical plane R while the state in which the optical axis of the first image capture device 3 is coaxial with the optical axis L1 of the first light source 2 is maintained. Therefore, in the defect inspecting apparatus of this embodiment, by the adjustment of the optical axis L1 of the first light source 2, a fear that the optical axis of the first image capture device 3 may become non-coaxial with the optical axis L1 of the first light source 2 is eliminated, so that the adjustment for making the optical axis of the first image capture device 3 coaxial with the optical axis L1 of the first light source 2 is unnecessary.

Also, the light source member 4 is used as both of the second light source and the third light source. Therefore, the defect inspecting apparatus of this embodiment need not be provided with two light sources (the second light source and the third light source) independently and separately. Similarly, the image capture device 5 is used as both of the second image capture device and the third image capture device. Therefore, the defect inspecting apparatus of this embodiment need not be provided with two image capture devices (the second image capture device and the third image capture device) independently and separately. For this reason, the number of parts of the defect inspecting apparatus of this embodiment is small.

Since the first image capture device 3 and the image capture device 5 each are provided with a telecentric lens, even if the distances between the first image capture device 3 and the image capture device 5 and the outer peripheral surface of the lip part 102, and the load face 103 and the thread bottom face inspection zone 106, respectively, vary, distortion can be restrained from occurring in the captured images grabbed by the first image capture device 3 and the image capture device 5. Therefore, for the defect inspecting apparatus of this embodiment, even if the distances between the first image capture device 3 and the image capture device 5 and the outer peripheral surface of the lip part 102, and the load face 103 and the thread bottom face inspection zone 106, respectively, vary, defects on the outer peripheral surface of the lip part 102, on the load face 103, and in the thread bottom face inspection zone 106 can be inspected.

Also, in the defect inspecting apparatus of this embodiment, even if the directions of the optical axes of the light source member 4 and the image capture device 5 are inclined inwardly or outwardly in the pipe axis direction P relative to the vertical plane R, by the adjustment of the orientation of the mirror 6, the load face 103 or the thread bottom face inspection zone 106 can be illuminated by the light source member 4, and also the reflection light reflected by the load face 103 or the thread bottom face inspection zone 106 can be received by the image capture device 5. Therefore, if the optical axes of the light source member 4 and the image capture device 5 are inclined outwardly in the pipe axis direction P in the same way as the first image capture device 3 as in this embodiment, defects on the outer peripheral surface of the lip part 102, on the load face 103, and in the thread bottom face inspection zone 106 can be inspected, and also the defect inspecting apparatus of this embodiment can be made compact in size.

Also, it is preferable that the optical axis of the image capture device 5 at the time when the image capture device 5 functions as the second image capture device be adjusted so that the reflection light reflected to the direction inclined through c°, which is the largest angle in relation to the vertical plane R among the angles that the angle B satisfying formula (2) can take, can be received. If the direction of the optical axis of the image capture device 5 is adjusted so that the reflection light reflected to the direction such that the angle in relation to the pipe axis direction P is small can be received, the image capture range of the image capture device 5 can be widened along the pipe axis direction P. Therefore, by adjusting the optical axis of the image capture device 5 so that the reflection light reflected to the direction inclined through c° can be received, the images of many load faces 103 can be grabbed by one image capture process. Also, it is preferable that the optical axis of the image capture device 5 at the time when the image capture device 5 functions as the third image capture device be adjusted so that the reflection light reflected to the direction inclined through d°, which is the smallest angle in relation to the pipe axis direction P among the angles that the angle C satisfying formula (3) can take, can be received. If the direction of the optical axis of the image capture device 5 is adjusted so that the reflection light reflected to the direction such that the angle in relation to the pipe axis direction P is small can be received, the image capture range of the image capture device 5 can be widened along the pipe axis direction P. Therefore, by adjusting the optical axis of the image capture device 5 so that the reflection light reflected to the direction inclined through d° can be received, the images of many thread bottom face inspection zones 106 can be grabbed by one image capture process. By adjusting the optical axis of the image capture device 5 in this manner, defects on the load face 103 and in the thread bottom face inspection zone 106 can be inspected by a small number of image captures, and the inspection time of the load face 103 and the thread bottom face inspection zone 106 can be shortened.

Second Embodiment

The defect inspecting apparatus of a second embodiment includes a fourth light source in place of the light source member in the first embodiment, and includes a fourth image capture device in place of the image capture device of the first embodiment. The fourth light source illuminates the load face 103 and in the thread bottom face inspection zone 106 at the same time. The fourth image capture device is attached to the fourth light source. The fourth image capture device is an image capture device that has the optical axis adjusted so that the reflection lights that are emitted from the fourth light source and reflected by the load face 103 and the thread bottom face inspection zone 106 to the direction inclined through the angle C satisfying formula (3) inwardly in the pipe axis direction P relative to the vertical plane R can be received, and the reflection lights are received to grab the images of the load face 103 and the thread bottom face inspection zone 106.

As described above, for the image capture device of the first embodiment, the reflection light reflected by the load face 103 can be received by adjusting the optical axis so that the reflection light reflected to the direction inclined through the angle B inwardly in the pipe axis direction P relative to the vertical plane R can be received. The lower limits of the angle B and the angle C are equal to each other, being b°, but the upper limit d° of the angle C is smaller than the upper limit c° of the angle B. Therefore, the range of the angle C is included in the range of the angle B. For this reason, the fourth image capture device the optical axis of which is adjusted so as to be capable of receiving the reflection lights reflected by the load face 103 and the thread bottom face inspection zone 106 to the direction inclined through the angle C inwardly in the pipe axis direction P relative to the vertical plane R can simultaneously receive the reflection lights reflected by respective positions of the load face 103 and the thread bottom face inspection zone 106. For the fourth image capture device, by simultaneously receiving the reflection lights reflected by respective positions of the load face 103 and the thread bottom face inspection zone 106, the images of both the load face 103 and the thread bottom face inspection zone 106 can be grabbed by one image capture process. Therefore, according to the defect inspecting apparatus of this embodiment, defects on the load face 103 and in the thread bottom face inspection zone 106 can be inspected by a small number of image captures, and the inspection time of the load face 103 and the thread bottom face inspection zone 106 can be shortened.

Third Embodiment

Figure 9:
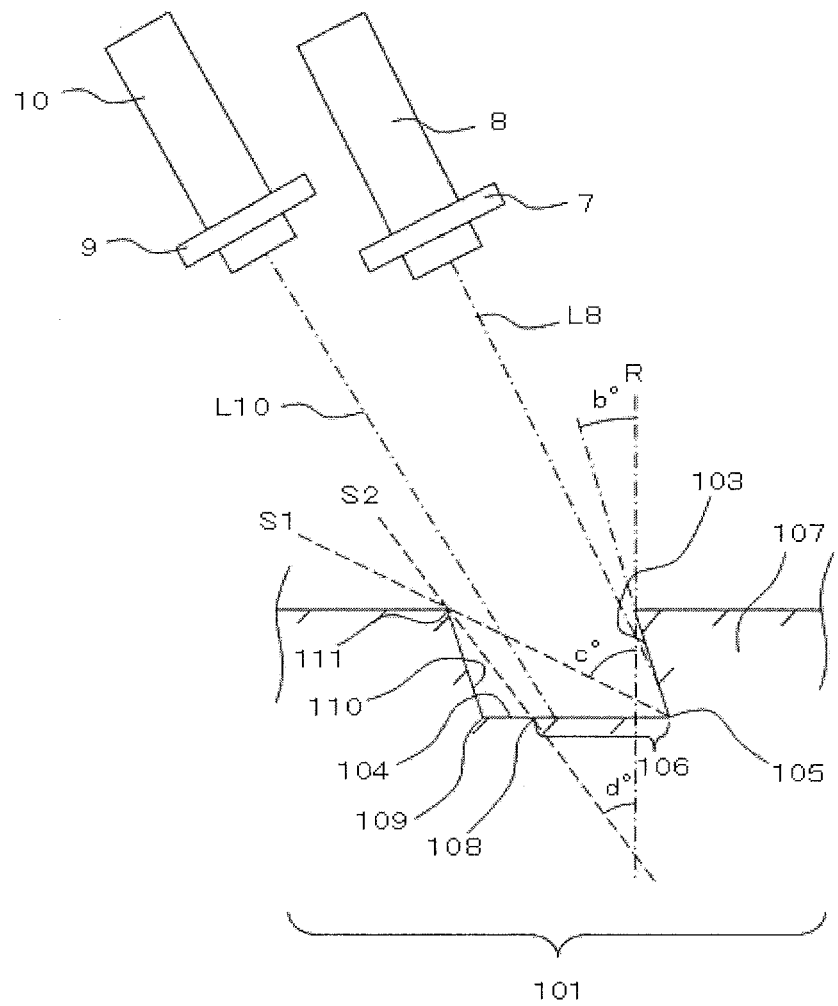
FIG. 9 is a view showing a schematic configuration of a defect inspecting apparatus of a third embodiment of the present invention, showing a cross section including the inspected pipe axis.
Figure 10:
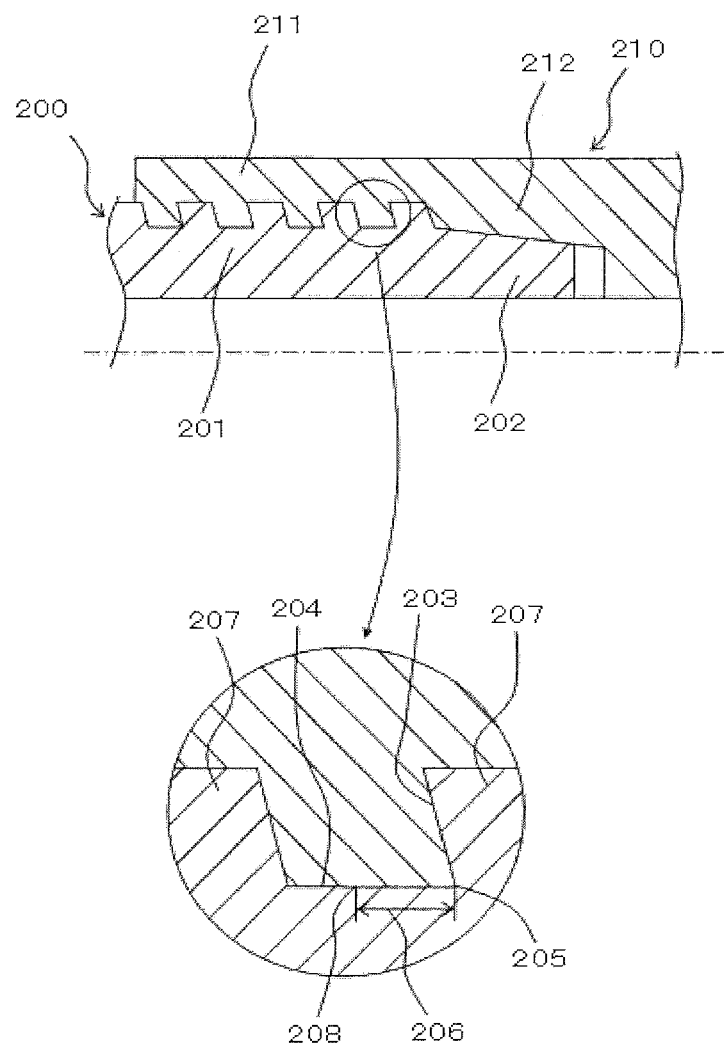
FIG. 10 is a sectional view of an oil well steel pipe and a joint.
Figure 11:
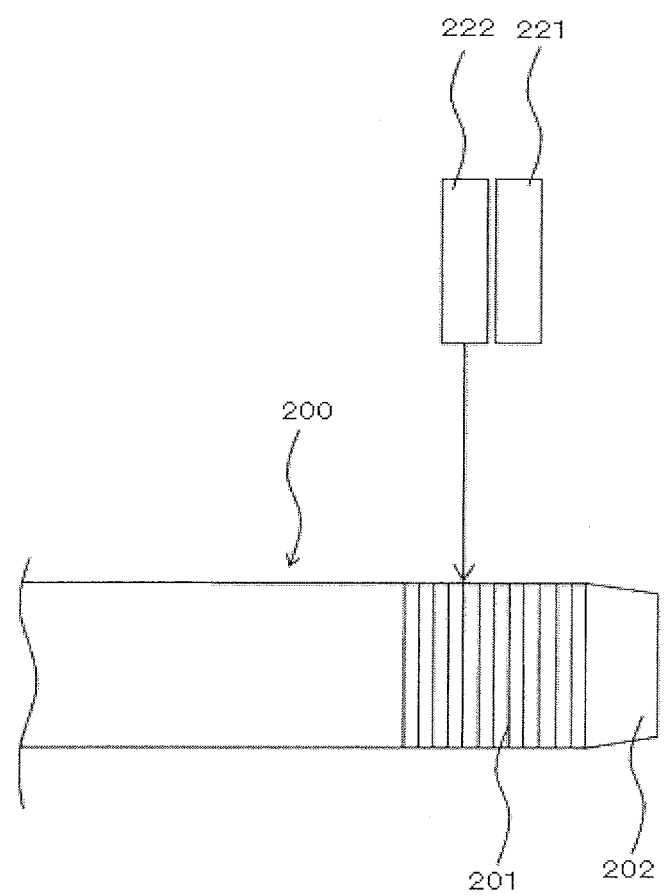
FIG. 11 is a schematic view of a conventional defect inspecting apparatus.

As shown in FIG. 9, the defect inspecting apparatus 1 of a third embodiment includes the first light source 2 (not shown), the first image capture device 3 (not shown), a second light source 7, a second image capture device 8, a third light source 9, a third image capture device 10, and the inspection device (not shown). The first light source 2, the first image capture device 3, and the inspection device each have the same configuration as that in the defect inspecting apparatus of the first embodiment.

The second light source 7 is a light source for illuminating the load face 103. The second image capture device 8 is attached to the second light source 7 and receives the light reflected by the load face 103. The optical axis of the second image capture device 8 is adjusted to the direction inclined through the angle B satisfying formula (2) inwardly in the pipe axis direction P relative to the vertical plane R. As described above, all the reflection lights reflected by the load face 103 are reflected by the load face 103 to the direction inclined through an angle larger than b° inwardly in the pipe axis direction relative to the vertical plane R. Also, if the reflection direction of the reflection light reflected by the above-described boundary part 105 is a direction inclined through an angle larger than the angle c° inwardly in the pipe axis direction P relative to the vertical plane R, the reflection light enters the insertion face 110. Therefore, the second image capture device 8 can receive the reflection light reflected by the load face 103, and therefore can grab the image of the load face 103.

The third light source 9 is a light source for illuminating the thread bottom face inspection zone 106. The third image capture device 10 is attached to the third light source 9 and receives the light reflected by the thread bottom face inspection zone 106. For the third image capture device 10, the direction of the optical axis is adjusted to the direction inclined through the angle C satisfying formula (3) inwardly in the pipe axis direction P relative to the vertical plane R. As described above, the reflection light reflected by the above-described boundary part 105 to the direction inclined through the angle b° or an angle smaller than b° inwardly in the pipe axis direction P relative to the vertical plane R enters the load face 103. Also, the reflection light reflected by the inside end part 108 in the pipe axis direction of the thread bottom face inspection zone 106 to the direction inclined through an angle larger than the angle d° inwardly in the pipe axis direction P relative to the vertical plane R enters the insertion face 110. Therefore, the third image capture device 10 can receive the reflection light reflected by the thread bottom face inspection zone 106, and therefore can grab the image of the thread bottom face inspection zone 106.

REFERENCE SIGNS LIST

2 . . . first light source, 3 . . . first image capture device, 4 . . . light source member, 5 . . . image capture device, 6 . . . mirror, 7 . . . second light source, 8 . . . second image capture device, 9 . . . third light source, 10 . . . third image capture device

The invention claimed is:

1. A defect inspecting apparatus for inspecting a defect on the outer peripheral surface of a pipe or tube in which in the end portion thereof, an external thread part and a lip part are provided in that order from the inside in the pipe or tube axis direction; a load face of the external thread part is inclined inwardly in the pipe or tube axis direction relative to the vertical plane perpendicular to the pipe or tube axis direction; and the lip part is tapered such that the dimension in the direction perpendicular to the pipe or tube axis direction decreases outwardly in the pipe or tube axis direction, the defect inspecting apparatus comprising:

a first light source for illuminating the outer peripheral surface of the lip part, in which the optical axis thereof is inclined through an angle A satisfying formula (1) outwardly in the pipe or tube axis direction relative to the vertical plane;

a first image capture device which is attached to the first light source so that the optical axis thereof is coaxial with the optical axis of the first light source, and receives the reflection light emitted from the first light source and reflected by the outer peripheral surface of the lip part to grab the image of the outer peripheral surface of the lip part;

a second light source for illuminating the load face;

a second image capture device which is attached to the second light source, and has the optical axis adjusted so that the reflection light emitted from the second light source and reflected by the load face to the direction inclined through an angle B satisfying formula (2) inwardly in the pipe or tube axis direction relative to the vertical plane can be received, and the reflection light is received to grab the image of the load face;

a third light source for illuminating a thread bottom face inspection zone ranging from a boundary part between the load face and the thread bottom face of the external thread part to a portion of the thread bottom face spaced apart inwardly by a predetermined distance from the boundary part in the pipe or tube axis direction;

a third image capture device which is attached to the third light source, and has the optical axis adjusted so that the reflection light emitted from the third light source and reflected by the thread bottom face inspection zone to the direction inclined through an angle C satisfying formula (3) inwardly in the pipe or tube axis direction relative to the vertical plane can be received, and the reflection light is received to grab the image of the thread bottom face inspection zone; and an inspection device for inspecting defects on the outer peripheral surface of the lip part, on the load face, and in the thread bottom face inspection zone by processing the captured images grabbed by the first to third image capture devices:

$$a-45 \leq A \leq a+45 \tag{1}$$

$$b < B \leq c \tag{2}$$

$$b < C \leq d \tag{3}$$

a° being an angle (smaller than 90°) formed between the outer peripheral surface of the lip part and the pipe or tube axis direction in the cross section including the pipe or tube axis;

b° being an angle (smaller than 90°) formed between the load face and the vertical plane in the cross section including the pipe or tube axis;

c° being an angle (smaller than 90°) formed between a straight line and the vertical plane in the cross section including the pipe or tube axis, the straight line connecting the boundary part between the load face and the thread bottom face to a front end part of an insertion face of the external thread part, the insertion face connecting with an inside end part in the pipe or tube axis direction of the thread bottom face; and d° being an angle (smaller than 90°) formed between a straight line and the vertical plane in the cross section including the pipe or tube axis, the straight line connecting an inside end part in the pipe or tube axis direction of the thread bottom face inspection zone to the front end part of the insertion face of the external thread part, the insertion face connecting with an inside end part in the pipe or tube axis direction of the thread bottom face.

2. The defect inspecting apparatus according to claim 1, comprising:
a single light source member used as both of the second light source and the third light source;
a single image capture device used as both of the second image capture device and the third image capture device; and
a mirror the orientation of which can be changed over between an orientation at which the light emitted from the light source member is caused to enter the load face and the reflection light emitted from the light source member and reflected by the load face is received by the image capture device and an orientation at which the light emitted from the light source member is caused to enter the thread bottom face inspection zone and the reflection light emitted from the light source member and reflected by the thread bottom face inspection zone is received by the image capture device.

3. The defect inspecting apparatus according to claim 1, wherein
the first image capture device is provided with a telecentric lens for receiving the reflection light reflected by the outer peripheral surface of the lip part;
the second image capture device is provided with a telecentric lens for receiving the reflection light reflected by the load face; and
the third image capture device is provided with a telecentric lens for receiving the reflection light reflected by the thread bottom face inspection zone.

4. The defect inspecting apparatus according to claim 1, wherein
the first light source is a ring-shaped illuminator attached around the first image capture device;
the second light source is a ring-shaped illuminator which has an optical axis coaxial with the optical axis of the second image capture device and is attached around the second image capture device; and
the third light source is a ring-shaped illuminator which has an optical axis coaxial with the optical axis of the third image capture device and is attached around the third image capture device.

5. The defect inspecting apparatus according to claim 1, comprising:
a fourth light source in place of the second light source and the third light source; and
a fourth image capture device in place of the second image capture device and the third image capture device, wherein
the fourth light source illuminates the load face and the thread bottom face inspection zone; and
the fourth image capture device is attached to the fourth light source, and has the optical axis adjusted so that the reflection light which is emitted from the fourth light source and reflected by the load face to the direction inclined through the angle C satisfying formula (3) inwardly in the pipe or tube axis direction relative to the vertical plane and the reflection light which is emitted from the fourth light source and reflected by the thread bottom face inspection zone to the direction inclined through the angle C satisfying formula (3) inwardly in the pipe or tube axis direction relative to the vertical plane can be received, and the reflection lights are received to grab the images of the load face and the thread bottom face inspection zone; and
the inspection device inspects defects on the outer peripheral surface of the lip part, on the load face, and in the thread bottom face inspection zone by processing the captured images grabbed by the first and fourth image capture devices in place of the captured images grabbed by the first to third image capture devices:

$$b < C \leq d \tag{3}$$

b° being an angle (smaller than 90°) formed between the load face and the vertical plane in the cross section of the pipe or tube including the pipe or tube axis; and d° being an angle (smaller than 90°) formed between a straight line and the vertical plane in the cross section of the pipe or tube including the pipe or tube axis, the straight line connecting a rear end part of the thread bottom face inspection zone on a thread bottom face to a front end part of an insertion face of the external thread part, the insertion face connecting with an inside end part in the pipe or tube axis direction of the thread bottom face.

6. The defect inspecting apparatus according to claim 5, wherein
the first image capture device is provided with a telecentric lens for receiving the reflection light reflected by the outer peripheral surface of the lip part; and
the fourth image capture device is provided with a telecentric lens for receiving the reflection light reflected by the load face and the reflection light reflected by the thread bottom face inspection zone.

7. The defect inspecting apparatus according to claim 5, wherein
the first light source is a ring-shaped illuminator attached around the first image capture device; and
the fourth light source is a ring-shaped illuminator which has an optical axis coaxial with the optical axis of the fourth image capture device and is attached around the fourth image capture device.

* * * * *